United States Patent
Kerschhacker et al.

(10) Patent No.: US 8,576,397 B2
(45) Date of Patent: Nov. 5, 2013

(54) DEVICE AND METHOD FOR DETERMINING A GAS CONCENTRATION IN A FLOWING GAS MIXTURE

(75) Inventors: Markus Kerschhacker, St. Radegund (AT); Johann Huber, Burghausen (DE); Markus Niemetz, St. Radegund (AT); Christoph Maurer, Ueberackern (AT)

(73) Assignee: Wacker Chemie AG, Munich (DE)

( * ) Notice: Subject to any disclaimer, the term of this patent is extended or adjusted under 35 U.S.C. 154(b) by 35 days.

(21) Appl. No.: 13/398,898

(22) Filed: Feb. 17, 2012

(65) Prior Publication Data

US 2012/0218552 A1   Aug. 30, 2012

(30) Foreign Application Priority Data

Feb. 25, 2011 (DE) .......................... 10 2011 004 744

(51) Int. Cl.
*G01N 21/59* (2006.01)

(52) U.S. Cl.
USPC .......................................................... 356/437

(58) Field of Classification Search
USPC .......................................................... 356/437
See application file for complete search history.

(56) References Cited

U.S. PATENT DOCUMENTS

| | | | |
|---|---|---|---|
| 4,108,964 A | 8/1978 | Kratel et al. | |
| 4,709,150 A | 11/1987 | Burough et al. | |
| 5,384,640 A | 1/1995 | Wong | |
| 6,064,488 A | 5/2000 | Brand et al. | |
| 6,322,765 B1 | 11/2001 | Muehlhofer et al. | |
| 2007/0186622 A1* | 8/2007 | Firon et al. .......................... 73/38 | |

FOREIGN PATENT DOCUMENTS

| | | |
|---|---|---|
| CN | 100545634 C | 9/2009 |
| DE | 2620737 A1 | 12/1977 |
| EP | 0790213 A1 | 8/1997 |
| GB | 2262338 A | 6/1993 |
| JP | 61108947 A | 5/1986 |
| JP | 5052754 A | 3/1993 |
| JP | 2005512052 A | 4/2005 |
| JP | 2007506974 A | 3/2007 |
| JP | 2008196870 A | 8/2008 |

OTHER PUBLICATIONS

PatBase abstract for CN 100545634 C.

* cited by examiner

*Primary Examiner* — Tu Nguyen
(74) *Attorney, Agent, or Firm* — Caesar, Rivise, Bernstein, Cohen & Pokotilow, Ltd.

(57) ABSTRACT

The invention relates to a method for determining a gas concentration in a flowing gas mixture, wherein the flowing gas mixture includes solids having a defined size distribution, wherein by way of an optical spectrometer the concentration of a gas is measured in the flowing gas mixture, which includes a measurement beam of the optical spectrometer being conducted during the measurement through a measurement channel having walls made of a gas-permeable material. The invention also relates to a device for carrying out such a method.

12 Claims, 1 Drawing Sheet

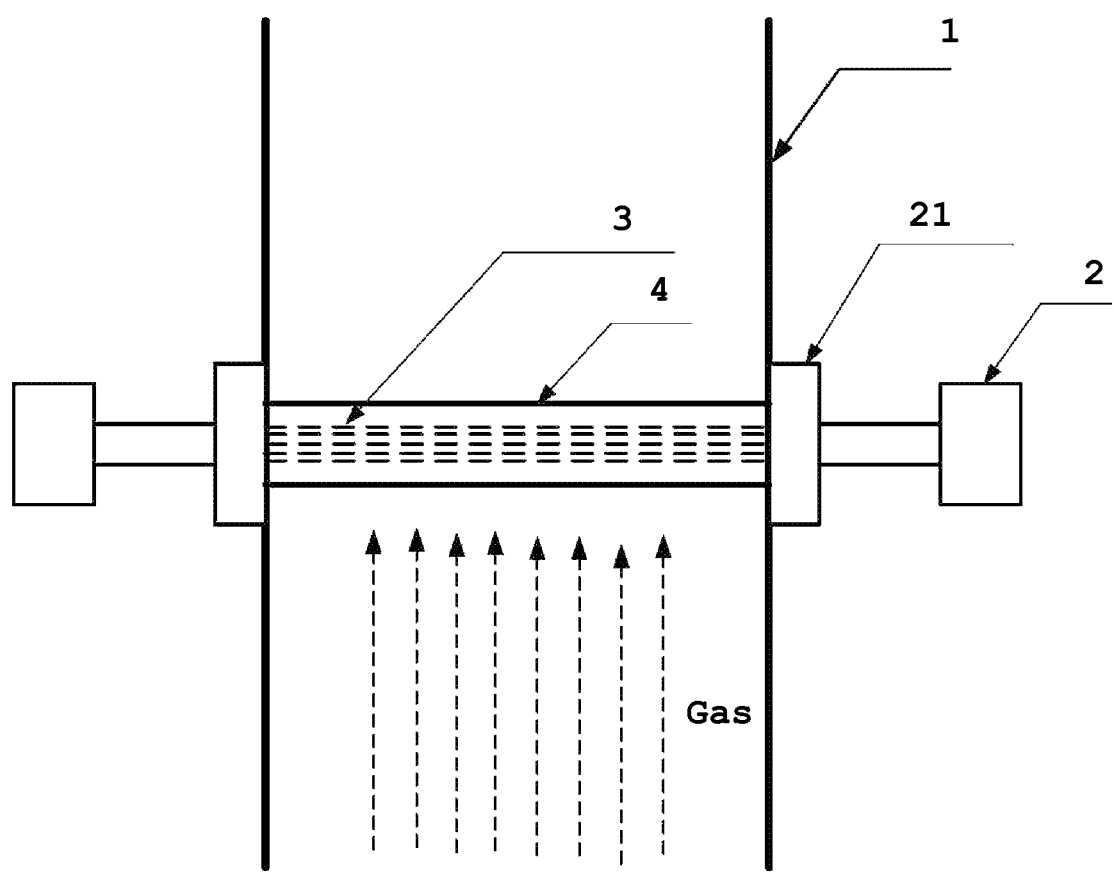

DEVICE AND METHOD FOR DETERMINING A GAS CONCENTRATION IN A FLOWING GAS MIXTURE

BACKGROUND OF THE INVENTION

The invention relates to a method for determining a gas concentration in a flowing, solids-containing gas mixture, and also to a device for carrying out such a method.

In the chemical industry it is frequently necessary, e.g., for process control, to determine the concentration of a gas in a solids-gas mixture. This proceeds, for example, toward the end of a process, in order to determine the fraction of a gas in a solids-containing product and starting material mixture before the product is separated from the unreacted residual starting materials or any byproducts and removed from a reactor. Likewise, the gas fraction can be determined during a reaction, in order, for example, to determine the fraction of a starting material gas or the fraction of a product gas in the reaction gas mixture.

Gas analyses of this type are also known from the fired-plant industry, since the operators of such systems are legally required to regularly demonstrate compliance with emission limiting values. In the case of measurements of the fractions of CO, NO, $NO_2$, $SO_2$, etc. in flue gas, for example paramagnetic oxygen measurement and nondispersive IR spectroscopy are used.

Particular attention is given in measuring technology to the determination of the gas concentration of oxygen. The importance of oxygen lies, in particular, in the control of a combustion process, monitoring of a reaction, or in safety aspects.

From the automobile industry, the exact oxygen measurement in exhaust gas is known using what is termed the lambda probe, in order to control the fuel-air mixture. Here, the fact that zirconium dioxide can transport oxygen ions electrolytically at high temperature is utilized, whereby a voltage is produced.

For oxygen measurements, therefore $ZrO_2$ probes come into consideration. This measurement is based on the fact that in a measurement cell a reference gas (e.g., air) is separated from the sample gas by a zirconium oxide membrane which is coated on both sides with platinum. An electrochemical cell is formed thereby, which, in the event of a difference in the oxygen concentrations on both sides, leads to an oxygen gradient over the thickness of the zirconium oxide membrane and to an electrical potential difference between the platinum electrodes. From the voltage drop, the oxygen partial pressure may be determined.

During the monitoring of heating boilers, a lambda probe can measure the oxygen content of the exhaust gas, and thus control at the boiler an optimum mixture in order to prevent an excess or deficit of combustion air.

However, in applications in gas streams having a high particle fraction and possibly substances which cause a cross sensitivity or give rise to aging of the probe, these probes are too susceptible and the plants operated with such probes are very maintenance-intensive.

A further possibility for oxygen measurement is diode laser spectrometers. A detector measures the absorption of the laser light by the gas molecules. The gas concentration may be calculated therefrom.

However, the use of a diode laser spectrometer is always a problem if a process gas is to be studied that has a comparatively high solids fraction. The solids impair the transmission of the laser and thereby the measurement result.

Therefore, in the prior art, efforts have been taken to improve the concentration measurement in gases loaded with solid.

In CN 100545634C, for this purpose, the use of displacement bodies or blocking systems is proposed, in order to deflect or block the solid particles. The displacement bodies have, for example, the shape of baffle plates. However, it has been found that in dilute solids-gas streams and certain highly fluid solids, owing to vortex formation and reverse streams, solids can pass onto and behind the baffle plates, and here also the laser beam is impaired.

Conventional laser spectrometers can only be operated reliably in the case of gas mixtures having a particle fraction up to approximately 50 $g/m^3$.

However, in the chemical industry there are applications in which the particle fraction is markedly higher.

One example thereof is process control in the production of highly dispersed silica.

In the production of polycrystalline silicon by deposition from chlorosilanes and hydrogen, e.g. in a Siemens reactor, silicon tetrachloride ($SiCl_4$) arises.

The production of $SiO_2$ powders (highly dispersed silica) via flame hydrolysis is known, for example, from DE2620737 and EP790213. In addition to the abovementioned silicon tetrachloride, a multiplicity of other silicon-containing compounds and mixtures thereof can also serve as feedstocks, e.g., methyltrichlorosilane, trichlorosilane or mixtures thereof with silicon tetrachloride. Chlorine-free silanes or siloxanes can also be used. According to EP790213, the use of dimeric chlorosilanes and siloxanes is also possible.

For process control and safeguarding, oxygen measurements are required in the production of silica.

In the production of silica, the gas stream usually comprises a particle fraction of greater than 50 $g/m^3$, usually 100-200 $g/m^3$.

This means that without additional devices, measurement of gas concentrations by way of conventional optical measurement technology, such as, for example, oxygen measurement by way of laser technology, is not possible.

The displacement bodies proposed in CN 100545634C, when employed in the production of silica produced by flame hydrolysis, lead to uncertain measurement results. This is associated, firstly, with the size and density of the particles present in the gas stream. Also the extremely low inertia of the particles has proved to be disadvantageous for the measurement. The laser measurement is impaired by the displacement bodies, owing to vortex formation, not being able to ensure that no particles pass into the measurement section. The transmission of the laser is too low in such a gas stream. Especially in the production of silica by means of flame hydrolysis, lasers, having too low a transmission value, are not permitted by the technical inspection agency as a protective appliance against the formation of ignitable gas mixtures.

The object of the present invention resulted from these problems.

DESCRIPTION OF THE INVENTION

The object of the invention is achieved by a method for determining a gas concentration in a flowing gas mixture, wherein the flowing gas mixture comprises solids having a defined size distribution, wherein by way of an optical spectrometer the concentration of a gas is measured in the flowing gas mixture, which comprises a measurement beam of the optical spectrometer being conducted during the measurement through a measurement channel having walls made of a gas-permeable material.

The invention further relates to a device for determining a gas concentration of a solids-containing gas mixture of an industrial plant, which device comprises a gas line, suitable for conducting a solids-containing gas mixture, an optical spectrometer, within the gas line a measurement channel comprising a measurement beam of the optical spectrometer, wherein the measurement channel is surrounded by walls made of a gas-permeable material.

The invention further relates to the use of hollow cylinders made of a gas-permeable material for shielding a measurement beam of an optical spectrometer from solids in a flowing solids-gas mixture.

The optical spectrometer is preferably a laser spectrometer.

The measurement beam is preferably a laser beam.

The industrial plant is preferably a reactor. This reactor preferably comprises a feed device for reaction gases, a reaction chamber and an outlet device for product gases.

The measurement channel can be situated within and outside the reactor.

The material of the walls of the measurement channel or of the hollow cylinder is of such a nature that it is optimally matched to the particle-gas conditions.

Preferably, the measurement channel is formed by a cylindrical body. Cylindrical in the context of the invention means that the body comprises a shell surface and a cross section, wherein the cross section can be, for example, circular or rectangular.

The measurement channel can be given, for example, by the shape of a tube.

The cylindrical body which forms the measurement channel is preferably provided in a path of the process gas which this gas takes, e.g., in a reactor or in a (production) plant.

Preferably, the cylindrical body is mounted on a holder that makes possible simple removal of the body for maintenance purposes.

The length of the measurement channel (optical path length) can be selected so as to be variable, and it is preferably between 200 mm and a few meters.

The cross section of the measurement channel is preferably adapted to the optical system. The measurement beam of the optical spectrometer has a certain expanse. The cross section of the measurement channel shall be selected to be correspondingly greater. Preference is given to an internal diameter of the measurement channel at least 10% greater than a diameter of the measurement beam. The internal diameter of the measurement channel can be, for example, 3-100 mm, preferably 10-90 mm, particularly preferably 20-80 mm, very particularly preferably 30-70 mm.

The walls of the measurement channel should have a thickness such that they can withstand the forces caused by the flowing process gas.

Preferably, the wall thickness is 1 to 20 mm, particularly preferably 4 to 10 mm.

The gas permeability of the walls of the measurement channel is preferably 0.01 m/(s·bar)–0.1 m/(s·bar).

Preferably, the gas-permeable material is a porous material, the pore size of which is selected in dependence on the size distribution of the particles or solids in the gas mixture.

If the particles have, for example, a size distribution of 5 to 20 μm, the median pore size of the material should ideally be less than or equal to 5 μm.

As gas-permeable material, preferably a polymer is used.

Particular preference is given to the use of polytetrafluoroethylene (PTFE). Preferably, the gas permeability of the measurement channel made of PTFE is preferably 0.03 m/(s·bar)–0.08 m/(s·bar), very particularly preferably 0.04 m/(s·bar)–0.07 m/(s·bar).

Very particular preference is given to the use of sintered PTFE.

Gas-permeable sintered ceramics or sintered metals are equally suitable. Use thereof is particularly preferred if the measurements are made on gas mixtures having temperatures of above or equal to 200° C.

Preferably, the temperature of the gas mixture during the measurement is from 0 to 1500° C. Particularly preferably, the temperature of the gas mixture is 120 to 1000° C.

By using such a measurement channel, the solids in the gas mixture are kept away from the laser beam. Gas can penetrate the walls; the solid particles are kept away. Depending on the pore size or gas permeability selected, small particles can partly penetrate the walls of the measurement channel, but do not interfere with the measurement.

At the same time, it is ensured that the solids in the gas mixture cannot block the measurement channel.

Surprisingly, no deposits occur on the outer walls of the measurement channel.

The vortexing observed in the prior art, which contributed to an increase in the particle density, does not occur in the method according to the invention.

When the particles in the gas stream are comparatively light, that is, have a low inertia thereby, the particular advantages of the method are displayed, compared with the displacement bodies or baffle plates of the prior art. This is because the baffle plates can only fulfill their purpose when the particles are heavy enough in order to follow the baffle and not the flowing gas. However, this is not always the case in a multiplicity of applications.

More exact measurement of the gas concentration also gives an improved (faster) response behavior to process changes when the measurement serves for the control of a production process, which is preferred.

Preferably, corrosive or dust-, tar- or soot-containing gas mixtures are studied.

Preferably, the trace moisture in process gases is determined by way of the method.

Preferably, emissions in furnace systems are studied by way of the method.

Preferably, the concentration of a gas selected from the group consisting of $NH_3$, HCl, HF, $H_2S$, $O_2$, $H_2O$, CO, $CO_2$, NO, $NO_2$, $N_2O$, $CH_4$, $CH_2O$ and $C_2H_3Cl$ is determined. In addition, the concentration of halogens such as, e.g., chlorine or bromine, $SO_2$, $O_3$, organic gases (e.g. benzene, hydrogen peroxide, phenols, ketone, toluene) can be determined.

The absorption line of the gas that is to be determined can be in the entire wavelength range between IR and UV, preferably, the absorption line of the gas that is to be determined in the gas mixture is in the near IR range.

Very particular preference is given to determination of the oxygen concentration in a process gas.

Preferably, the concentration of oxygen is determined by way of the method according to the invention in a solids-loaded gas mixture.

Very particular preference is given to the use of the method in the context of flame hydrolysis of silica. The solids in the gas mixture in this case are flocculent aggregates of primary particles, or agglomerates of aggregates, wherein the agglomerates have a size from 1 to 250 μm. In this case, measurement serves for plant security and process control. The novel measurement method here has particular advantages, especially since the maintenance-intensive zirconium oxide probes can be replaced. The inventors have recognized that the zirconium oxide probes, in particular in the presence of HCl, which is the case in the flame hydrolysis of silica, deliver falsified measurement values. Measurement using a measurement channel having walls made of a gas-permeable material shows no problems at all in this respect.

The method according to the invention therefore represents a cheaper and more reliable measurement of the oxygen concentration in gas streams in the production of silica.

Other measures, such as a shortening of the measurement channel or of the measurement section, have proved to be unsuitable.

In the case of shortening of the measurement section, in order to reduce the number of the particles in this manner, the accuracy of measurement, owing to the shorter optical length, is only about 0.25% by volume, which is not acceptable in the measurement of low gas concentrations.

With respect to the displacement bodies described in the prior art, it has proved to be a further serious disadvantage that the pressure drops in the process gas channel markedly increase. This is associated with the reduction in cross section and also flows around the displacement bodies. In the method according to the invention, such pressure drops occur to a markedly lesser extent.

Experiments with a Pitot tube made of steel, in order to conduct away particle-free gas before measurement, were also not successful, since, firstly, in addition to the occurrence of corrosion problems, silica particles were also entrained. Secondly, a sufficient differential pressure for flow through the Pitot tube could not be provided, which caused very large dead periods, which in turn contradicted the safety requirements.

Experiments with filter bags made of PTFE needled felt, as are used in solids separation, were likewise unsuccessful in gas measurements in the context of flame hydrolysis of silica. Owing to the high flow velocity, silica particles were forced into the filter bag which blocked passage through the optical measurement beam. In addition, on the filter bag—owing to the high flow velocities in the process—mechanical abrasion was observable, which can lead to leaks of the filter.

Example

The cylindrical measurement channel is formed by a tube made of gas-permeable PTFE. The tube has a length of approximately 200 mm. The wall thickness is approximately 5 to 7 mm. The diameter of the tube is about 55 mm. The median pore size is 5 µm. The gas permeability of such PTFE tubes is in the range of 0.036 m/(s·bar)-0.073 m/(s·bar).

The gas permeability of a PTFE tube is ideally determined as follows:

The tube is sealed at both ends, e.g., with rubber stoppers, wherein one of the stoppers has an opening for pressure measurement and the other stopper has an opening for introducing air. The takeoff from a pressure line is reduced to 1.7 bar (in the case of a second comparison measurement to 1 bar). Using a controllable flow meter, the flow is set. Then the flow in the PTFE tube is measured using a relative pressure transmitter. The differential pressure over the tube may thereby be determined and finally the gas permeability calculated.

Such a PTFE tube is used in the example for measuring the oxygen concentration in a silica-containing gas mixture. As measuring instrument, a commercially conventional laser spectrometer is used for measuring gas concentrations in solids-containing gas mixtures. The temperature of the flowing gas mixture of which the oxygen concentration is measured is 167° C.

As test gas, an oxygen-nitrogen gas mixture containing 4.5% by volume of oxygen is fed to the silica at 80 g/m$^3$.

As a comparative example, instead of the filter tube, a baffle plate is used, as described in the prior art, cf. CN 100545634C.

Table 1 shows the results for example and comparative example.

TABLE 1

| Test structure | Starting values | | After 2 min | | After 5 min | | After 10 min | |
|---|---|---|---|---|---|---|---|---|
| | MW | Tr. | MW | Tr. | MW | Tr. | MW | Tr. |
| Comparative example | 4.50% by vol | 95% | 4.47% by vol | 25% | 3.11% by vol | 3% | no measurement | 1% |
| Example | 4.51% by vol | 94% | 4.50% by vol | 80% | 4.51% by vol | 79% | 4.49% by vol | 79% |

MW in the table designates the measured oxygen value in % by volume, Tr. the measured transmission of the laser beam in %.

It is found that only by using a filter tube which corresponds to a measurement channel according to the invention having walls made of a gas-permeable material, is sufficient transmission in the range of 80% achieved in a lasting manner. When a baffle plate is used, the transmission decreases even after 2 min to 25%. After 10 min, the transmission is already so low that an oxygen measurement is no longer possible.

A device for generating silica preferably comprises a reactor chamber of 1 to 40 m.

Preferably, the reactor chamber has a circular cross section. The reactor comprises a reaction nozzle having a preferably circular cross section.

The reaction gases are preferably oxygen, that is to say, for example, air, a combustion gas such as, for example, hydrogen, and a silicon compound.

Examples of the silicon compound are silicon tetrachloride, trichlorosilane, methylsilicon trichloride and mixtures thereof.

Preferably, the oxygen for use in the reactor is taken off from the air from the surrounding atmosphere. The oxygen $O_2$ in the air can be enriched to greater than 21% by volume, for example by addition of pure oxygen $O_2$ or by addition of air which contains greater than 21% by volume of oxygen $O_2$.

Preferably, via a further nozzle which encloses in an annular manner the reactor nozzle from which the reaction gases exit, pure oxygen or air or air-oxygen mixtures or, in addition, pure nitrogen or air or air-nitrogen mixtures or hydrogen or hydrogen-nitrogen mixture can additionally be fed.

Preferably, the hydrogen chloride that is formed in the reaction is recovered, purified and dried by absorption and possibly desorption. The method according to the invention is preferably also used for determining the concentration of hydrogen chloride in the process gases.

The dry hydrogen chloride thus obtained is preferably used for producing chlorosilanes such as trichlorosilane, dichlorosilane and monosilane from metallurgical silicon.

Preferably, reheating residual oxygen and chlorine gas is carried out by adding a combustion gas to the flame in the reactor chamber at at least one site different from the reactor nozzle.

Preferably, at various sites in the reaction chamber, further combustion gas such as, for example, hydrogen or natural gas, can be added into the reaction zone. Preferably, this additional combustion gas is used for reducing chlorine gas formed in the reactor to HCl.

Preferably, only hydrogen is used as combustion gas. Preferably, the formation of hydrocarbon oxides, such as carbon monoxide CO, and the formation of chlorinated aromatic hydrocarbons, such as, for example, chlorinated dibenzo-dioxins, is suppressed in this manner.

The concentration of carbon oxides such as carbon monoxide is preferably also determined using the method according to the invention.

BRIEF DESCRIPTION OF THE DRAWING

The invention will be described hereinafter with reference to FIG. 1.

FIG. 1 shows the device according to the invention schematically.

1 indicates a tube in which a gas mixture is transported. 3 is a measurement channel in which the concentration of a gas in the gas mixture is determined.

Measurement channel 3 is situated inside the filter tube 4, which comprises walls made of a gas-permeable porous material. The gas concentration is measured using an optical spectrometer 2 which is connected to measurement channel 3 via spectrometer accommodation 21.

What is claimed is:

1. A method for determining a gas concentration in a flowing gas mixture, wherein the flowing gas mixture comprises solids having a defined size distribution, said method comprising:
   providing an optical spectrometer adapted to generate a measurement beam;
   providing a measurement channel having walls made of a gas-permeable material;
   providing in the measurement channel a measurement beam from the optical spectrometer; and
   measuring with the measurement beam in the measurement channel the gas concentration of the flowing gas mixture penetrating through the walls of the measurement channel,
   wherein the flowing gas mixture comprises HCl, $Cl_2$, $O_2$ and flame hydrolyzed silica particles, and the concentration of oxygen or HCl is determined in the gas mixture.

2. The method as claimed in claim 1, wherein the gas-permeable material is a member selected from the group consisting of polymers, sintered ceramics and sintered metal.

3. The method as claimed in claim 1, wherein the gas-permeable material is polytetrafluoroethylene.

4. The method as claimed in claim 3, wherein the optical spectrometer is a laser spectrometer.

5. The method as claimed in claim 1, wherein the optical spectrometer is a laser spectrometer.

6. The method of claim 1, wherein the flowing gas mixture has a particle fraction of greater than 50 $g/m^3$.

7. The method of claim 6, wherein the particle fraction is 100-200 $g/m^3$.

8. The method of claim 1, wherein the gas permeability of the walls is 0.01 m/(s·bar)-0.1 m/(s·bar).

9. The method of claim 1, wherein outer walls of the measurement channel are free of deposits.

10. The method of claim 9, wherein the method is free of vortexing.

11. The method of claim 1, wherein the defined size distribution is 5 to 20 μm.

12. The method of claim 1, wherein: (a) the gas-permeable material is a member selected from the group consisting of polymers, sintered ceramics and sintered metal; (b) the flowing gas mixture has a particle fraction of greater than 50 $g/m^3$; (c) the gas permeability of the walls is 0.01 m/(s·bar)-0.1 m/(s·bar); (d) outer walls of the measurement channel are free of deposits; (e) the method is free of vortexing; and (f) the defined size distribution is 5 to 20 μm.

* * * * *